(12) United States Patent
Crain et al.

(10) Patent No.: US 6,644,852 B2
(45) Date of Patent: Nov. 11, 2003

(54) AUTOMATICALLY RECONFIGURABLE X-RAY POSITIONER

(75) Inventors: Michael M. Crain, Waukesha, WI (US); Daniel I. Kerpelman, Le Vesinet (FR)

(73) Assignee: GE Medical Systems Global Technology, Waukesha, WI (US)

( * ) Notice: Subject to any disclaimer, the term of this patent is extended or adjusted under 35 U.S.C. 154(b) by 0 days.

(21) Appl. No.: 10/063,815

(22) Filed: May 15, 2002

(65) Prior Publication Data

US 2003/0091156 A1 May 15, 2003

Related U.S. Application Data

(60) Provisional application No. 60/334,745, filed on Nov. 15, 2001.

(51) Int. Cl.$^7$ .................................................. H05G 1/02
(52) U.S. Cl. ........................................ 378/197; 378/193
(58) Field of Search .................................. 378/189, 193, 378/196, 197, 198, 98.2, 98.8

(56) References Cited

U.S. PATENT DOCUMENTS

| 4,894,855 A | | 1/1990 | Kresse ........................ 378/196 |
| 5,835,558 A | * | 11/1998 | Maschke ..................... 378/198 |
| 6,200,024 B1 | | 3/2001 | Negrelli ....................... 378/196 |
| 6,201,249 B1 | * | 3/2001 | Yamayoshi ............ 250/370.11 |
| 6,435,715 B1 | * | 8/2002 | Betz et al. ................... 378/197 |
| 6,453,004 B1 | * | 9/2002 | Albeniz et al. ................. 378/4 |

* cited by examiner

Primary Examiner—Drew A. Dunn
(74) Attorney, Agent, or Firm—Quarles & Brady LLP; Carl Horton

(57) ABSTRACT

Two independently articulated arms supporting an x-ray tube and x-ray detector, respectively, are mounted offset to the patient and controlled to simulate a wide variety of conventional x-ray positioners. The articulated arms provide for at least two axes of independent motion. An axis controller sends movement signals to each axis, and receives position signals from each axis to coordinate movement of the axes of the articulated arms according to a contained program. A network interface communicates with the axis controller for receiving at least a portion of the program over a network.

20 Claims, 6 Drawing Sheets

AUTOMATICALLY RECONFIGURABLE X-RAY POSITIONER

CROSS REFERENCE TO RELATED APPLICATIONS

The present application claims priority to U.S. Provisional Patent Application Ser. No. 60/334,745 and entitled "X-RAY POSITIONER WITH SIDE-MOUNTED, INDEPENDENTLY ARTICULATED ARMS" filed on Nov. 15, 2001, the disclosure of which is hereby incorporated by reference as if set forth in its entirety herein.

BACKGROUND OF INVENTION

This application relates to medical x-ray positioners and in particular to a positioner using independently articulated arms to support the x-ray source and x-ray detector.

Conventional x-ray positioners provide mechanical supports to hold an x-ray source and x-ray detector in opposition about a patient for a limited number of specific procedures. For procedures in which the patient is standing, the x-ray source may be attached to a pillar allowing adjustment in its height as directed toward an x-ray detector attached to an opposing wall or a second similar pillar. For procedures in which the patient is supine, the x-ray source and detector may be attached to opposite sides of a patient table. Alternatively, the x-ray source and the detector may be attached to opposite ends of a C-arm which is supported by a sliding collar allowing the angle of the x-rays through the patient to be varied.

Multi-axis robotic arms, positioned above and below the patient table, have been proposed to provide support for the x-ray source and x-ray detector such as may reduce interference between the support structure and other equipment and personnel. See, for example, U.S. Pat. No. 6,200,024 to Negrelli citing U.S. Pat. No. 4,894,855 to Kresse.

Such systems may emulate a standard x-ray positioner while eliminating supporting structure that might interfere with free movement of the positioner.

SUMMARY OF INVENTION

The present invention provides an x-ray machine using multi-axis articulated arms for holding the x-ray source and x-ray detector. Increased versatility in the operation of the x-ray machine of the present invention is provided by allowing programs and files necessary for the control of the arms to be downloaded to the x-ray machine from others.

The downloaded programs and data may include a "personality file" controlling the type of positioner emulated by the x-ray machine, a "configuration file" describing the capabilities of the x-ray machine, allowing it to be flexibly upgraded with additional axes and control options, a "zero configuration file" describing initialization of the x-ray machine for these different emulations, a "control map" translating operator control inputs to axis movement, and one or more "procedure engines" allowing semiautomatic execution of complex x-ray procedures including movement of the axes, techniques and image processing. These files may be exchanged over the Internet or the like.

DETAILED DESCRIPTION

Figure 1:
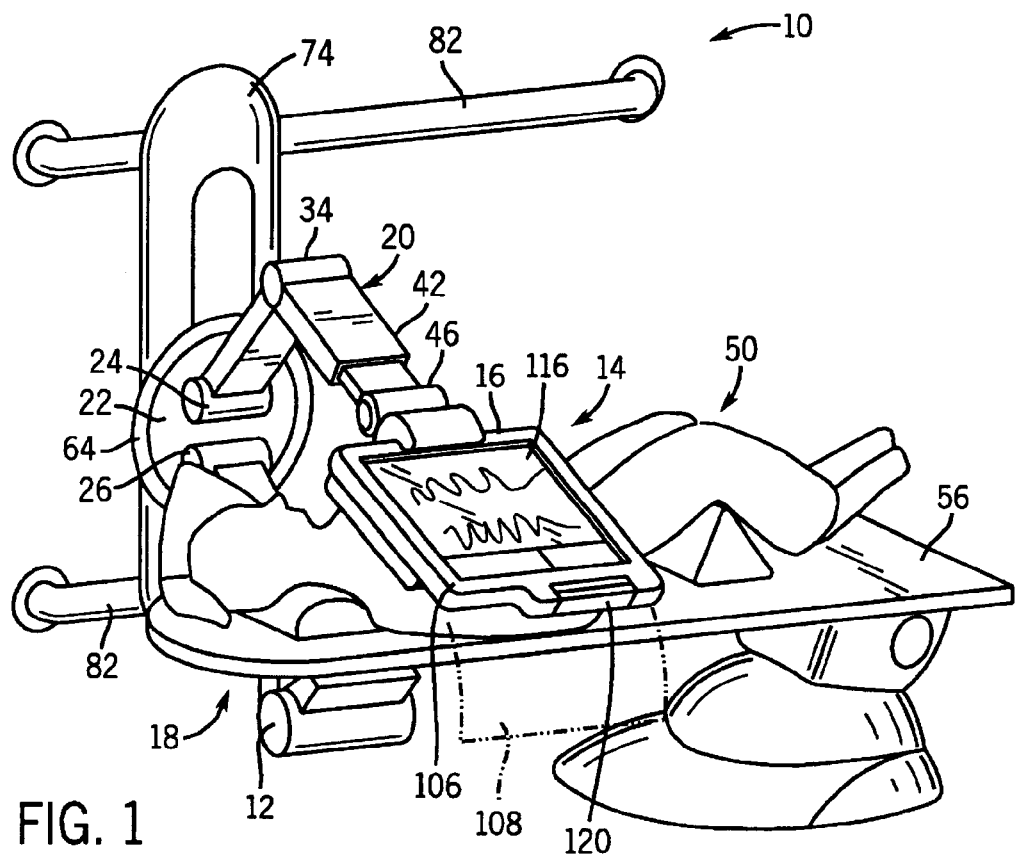
FIG. 1 is a perspective view of one embodiment of the positioner of the present invention showing offset mounting of two independently articulated arms holding an x-ray source and x-ray detector assembly, respectively.

Referring now to FIG. 1, a multi-mode x-ray positioner 10 per the present invention provides an x-ray source 12 and an x-ray detector 14. The x-ray source 12 generally includes an x-ray tube, the necessary cooling components, collimators, and shielding as will be understood to those of ordinary skill in the art. The x-ray detector 14 may be a lightweight flat panel detector such as may be fabricated as an array of detectors, an amorphous silicon detector panel or other imaging device. The x-ray detector is part of a detector assembly 16 to be described in greater detail below.

The x-ray source 12 directs an x-ray beam generally along a central ray 13 whereas the x-ray detector 14 receives x-rays generally along a central ray 15 normal to the surface thereof. A patient 50 may be supported supine on a table 56 so as to be aligned with the central rays 13 and 15. For this purpose, the table 56 is composed of a radiotranslucent material of a type well known in the art.

Figure 4:
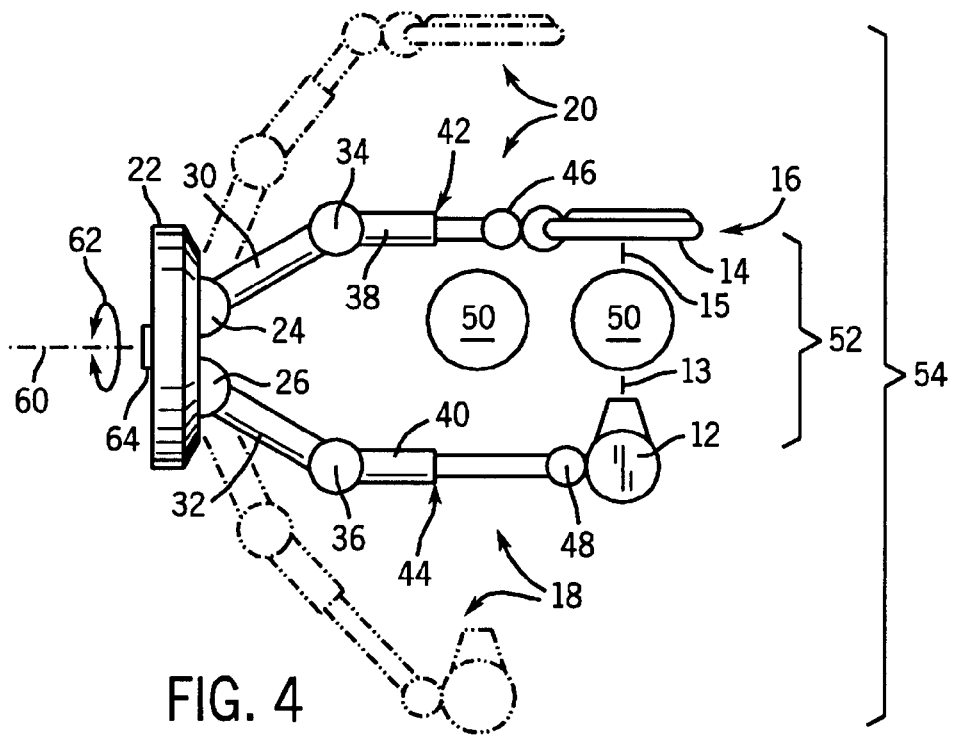
FIG. 4 is a view (top or side) of the articulated arms of the FIG. 1 showing, in phantom, arm movement implementing an increased source-to-detector distance.

Referring also to FIG. 4, each of the x-ray source 12 and the x-ray detector 14 are held, respectively, on separate articulated robot arms 18 and 20. The arms 18 and 20 are attached at a first end to a base 22, the latter preferably supported against a vertical surface with the arms extending laterally therefrom.

The arms 18 and 20 attach to the base 22 at shoulder axes 26 and 24, respectively. Each shoulder axes 26 and 24 provides angulation of its respective arm 18 or 20 about parallel axes extending generally along the plane of the base 22, the latter being parallel to a vertical plane defining the surface to which the base 22 is attached. Generally the term "axis" henceforth will refer both to a mechanical joint and the mathematical vector describing movement of that joint. The particular meaning will be evident from context.

Attached to and extending from shoulder axes 24 and 26 are upper arms 30 and 32, respectively, which terminate in elbow axes 34 and 36, respectively, each also providing for angulation along parallel axes also parallel to axes 24 and 26. Forearms 38 and 40 extend from elbow axes 34 and 36, respectively, and the latter which provide telescoping extension axes 42 and 44 permitting translation movement of wrist axes 46 and 48 along the length of the forearms 38 and 40.

Wrist axes 46 and 48 provide angulation about parallel axes also parallel to axes 24 and 26 and connect, respectively, to the x-ray detector assembly 16 and x-ray source 12. It is to be understood that the x-ray source and x-ray detector assembly are not limited to mounting on a particular arm and may be replaced by other devices to meet other clinical needs.

It will be understood from this description that each of the arms has four axes of motion comprised of shoulder axes 24, elbow axis 34 and wrist axis 46 and extension axis 42, for arm 20 and shoulder axes 26, elbow axis 36, and wrist axis 48, and extension axis 44 for arm 18. Generally, motion of shoulder axes 24 and 26 control the angle of upper arms 30 and 32 and the position of elbow axes 34 and 36 with respect to shoulder axes 24 and 26. Likewise, motion of elbow axes 34 and 36 control the angle of forearms 38 and 40 and the position of wrist axes 46 and 48 with respect to the elbow axes 34 and 36. Motion of extension axes 42 and 44 control the separation of elbow axis 34 and wrist axis 46 and elbow axis 36 and wrist axis 48, respectively, and motion of wrist axes 46 and 48 control the angle of detector 14 and x-ray source 12.

Each of axes 24, 26, 34, 36, 42, 44, 46, and 48 are enabled for servo control meaning that they may be moved electronically in response to a position signal received from the axis so that precise positioning and/or velocity control of each axis may be had through a central processor as will be described below.

Referring again to FIGS. 1 and 4, the arms 18 and 20 may be maneuvered to position the x-ray source 12 and detector assembly 16 in alignment on opposite sides of a patient 50 at a first source-to-detector distance 52. Subsequently, the arms 20 may be maneuvered, through a combined motion of their axes, to provide a source-to-detector distance 54 substantially greater than source-to-detector distance 52, while maintaining alignment. Such separation is accomplished principally by a combined angulation and extension of the axes 24, 26, 34, 36, 42, 44, 46, and 48 and notably does not require an axis of translation aligned with the central rays 13 and 15 of the source and detector as is typical of conventional x-ray positioners.

Referring again to FIGS. 1 and 4, the base 22 may be mounted on a waist axis 64 providing rotation about a line that is horizontal and perpendicular 60 to the plane of the base 22, the rotation as indicated by arrow 62. Thus, the arms 18 and 20 in their various source-to-detector separations 52 and 54 shown in FIG. 4 may be opposed about a substantially vertical axis (as depicted in FIG. 1) or about a horizontal axis. The horizontal axis is useful for procedures such as chest x-rays or other situations where the patient is best imaged while standing or seated. In these cases, the table 56 would be moved to a vertical configuration or moved out of the way altogether. The rotation of the base 22 about the waist axis 64, as with the other axes, is under servo control and provides single axis cranial-caudal angular adjustment.

Figure 5:
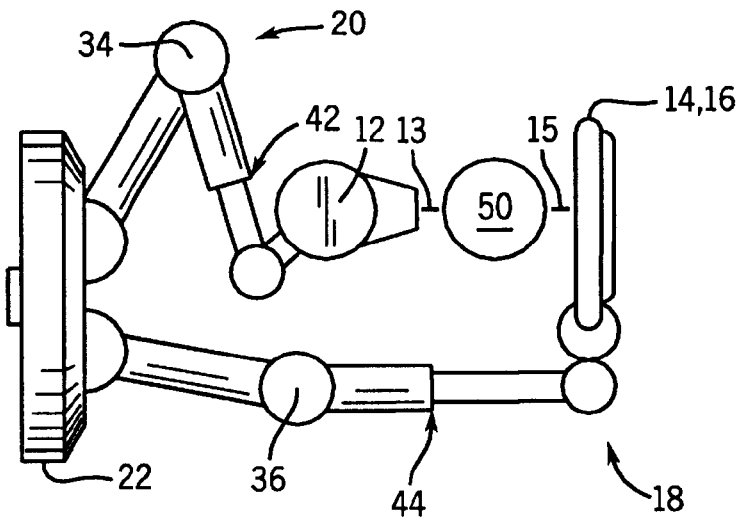
FIG. 5 is a side elevational viewing of the articulated arms of FIG. 1 showing positioning of the arms for lateral imaging.

Alternatively as shown in FIG. 5, the arms 18 and 20 may be manipulated to provide central rays 13 and 15 perpendicular to the plane of the base 22. In this case, the arms 18 and 20 are not deployed symmetrically but elbow axis 34 is moved to an acute position whereas elbow axis 36 is moved to an obtuse position with extension axis 44 fully extended and extension axis 42 fully retracted. This degree of flexibility is accomplished because each of the axes 24, 26, 34, 36, 44, 42, 46, and 48 are independently controllable.

Figure 6:
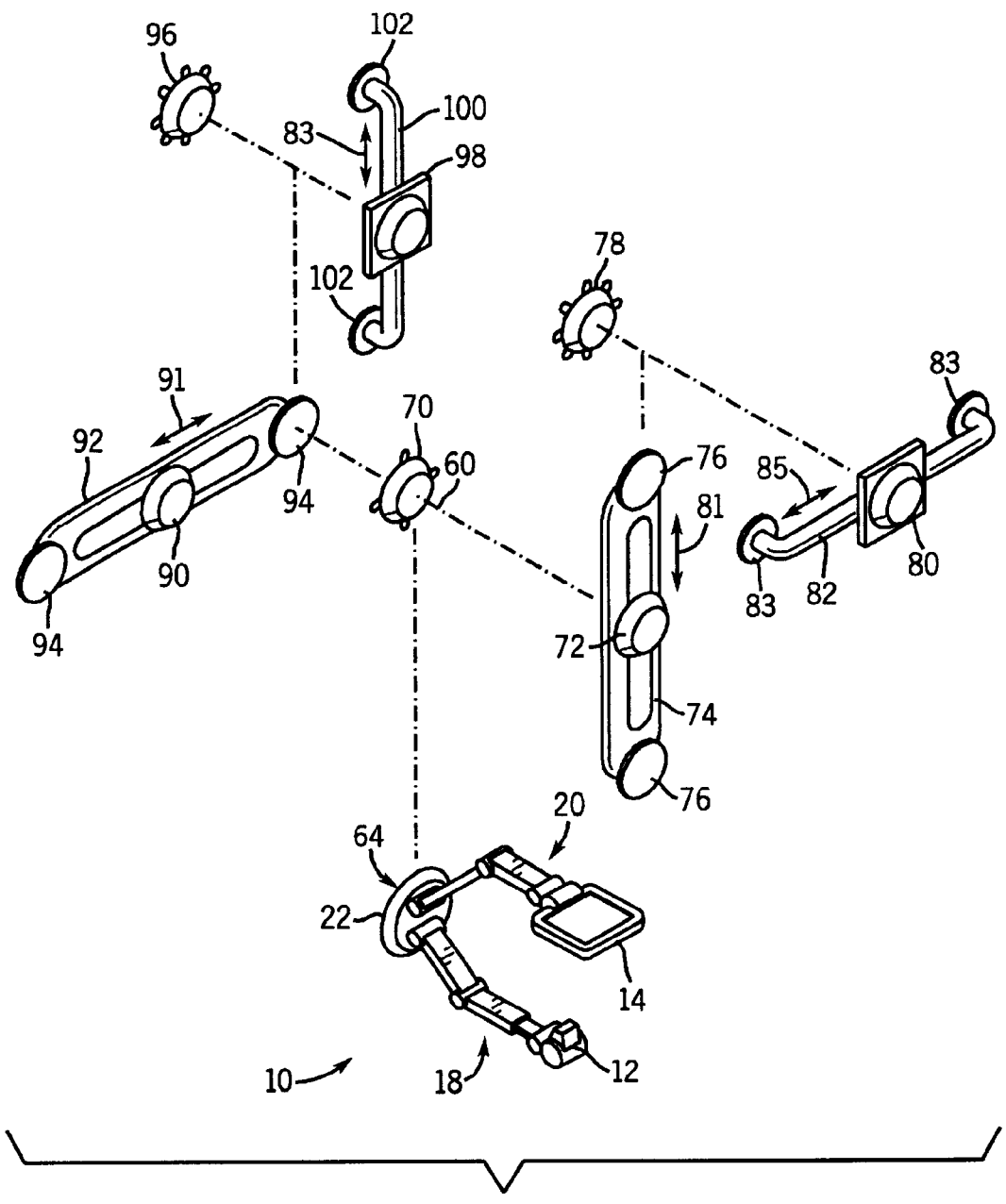
FIG. 6 is an exploded perspective diagram showing various options for adding common axes to the articulated arms of FIG. 1 for different procedures.

Referring to FIG. 6, the base 22 may be mounted directly on a wall or the like by means of stationary collar 70 receiving the waist axis 64. Alternatively, and as also shown in FIG. 1, the base 22 may be attached to a vertically translating collar 72 also receiving the waist axis 64 but providing for vertical translation along tracks 74 also under servo control to form translation axis 81. Opposed ends 76 of the track 74 may be held against the wall or vertical surface by stationary collars 78 (only one of which is shown for clarity) similar to stationary collar 70. The translation axis 81 allows single axis elevation of the x-ray source 12 and x-ray detector 16.

Alternatively, the end 76 may be received by horizontally translating collars 80 moving horizontally along tracks 82 so as to provide a horizontal servo control translation axis 85 for the tracks 74, the base 22, and thus the arms 18 and 20.

In an alternative configuration, the base 22 may be mounted to horizontally translating collar 90 of the tracks 92 positioned to extend horizontally along axis 91. The ends 94 of the tracks 92 may be attached either to a stationary collar 96, similar to stationary collars 78 or to horizontally vertically collars 98 but with the track 100 positioned to move along vertical axis 83, the latter having its ends 102 fixed to a stationary surface such as a wall or the like. The translation axis 91 allows single axis horizontal repositioning of the x-ray source 12 and x-ray detector 16.

While the two configurations represented in tree fashion by the branches ending with the axis 85 and 83 of FIG. 6 result in the same degrees of freedom, they provide alternate evolution paths allowing the positioner 10 to be upgraded from a base system having only base 22 and arms 18 and 20 to a full featured system through the addition, respectively, of various components of vertically translating collar 72, or horizontally translating collars 90. A wiring harness system (not shown) allows each of these axes to be added to an axis controller to provide improved functionality as will be described below.

Figure 2:
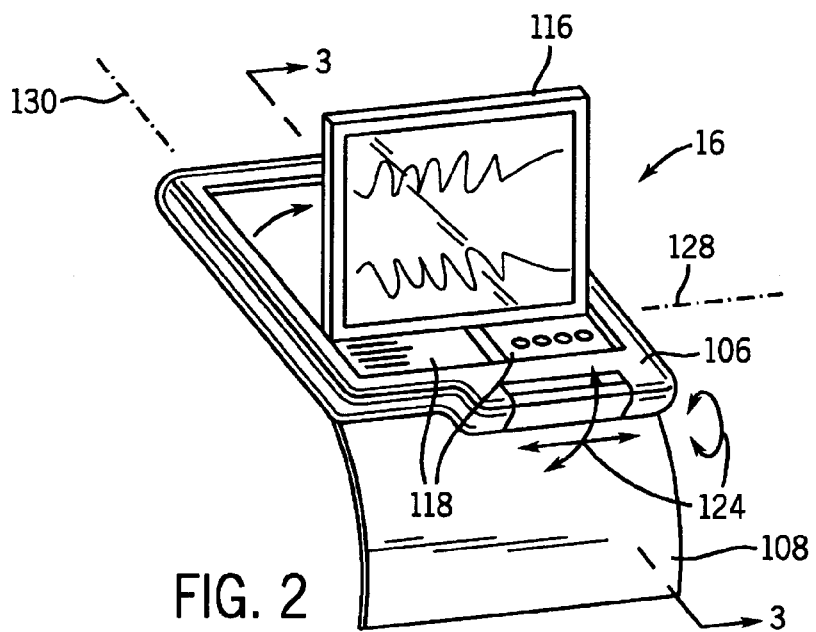
FIG. 2 is a perspective view of the detector of FIG. 1 showing a tilting upward of an integral display of the detector assembly and axes of movement of a control handle supported by the detector assembly.
Figure 3:
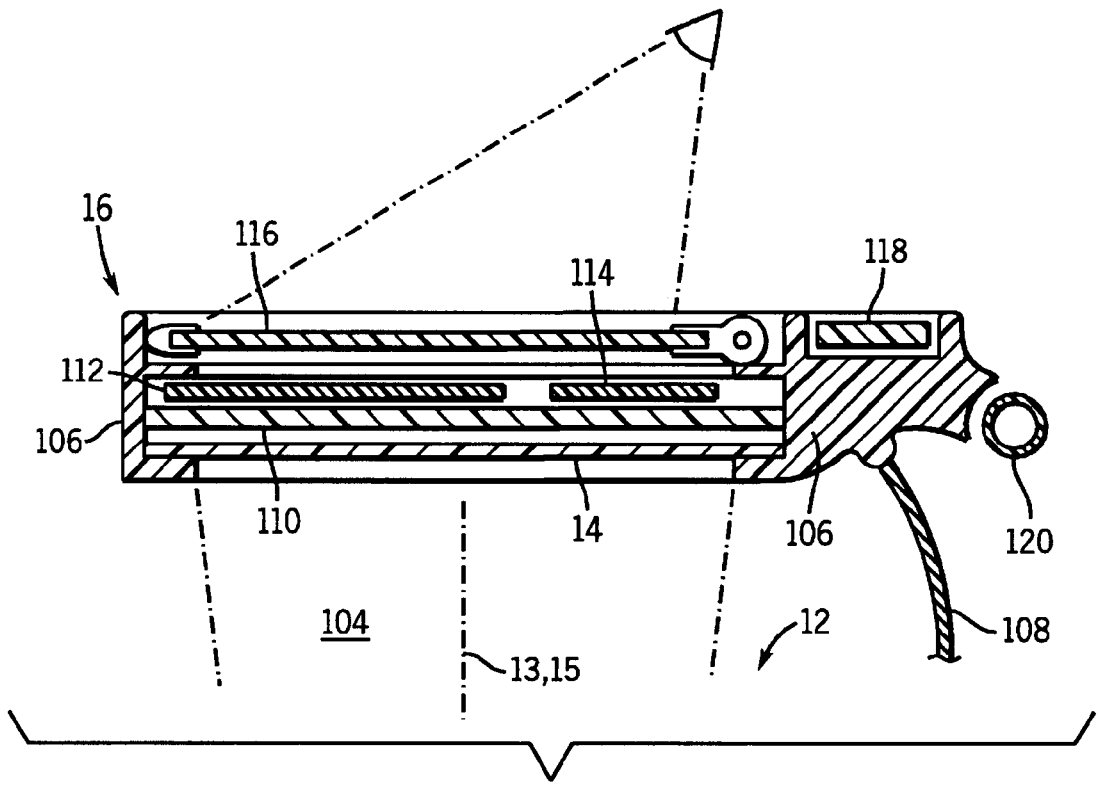
FIG. 3 is a cross-sectional view of the detector assembly of FIG. 2 taken along lines 3—3 of FIG. 2 showing the normal registration of an x-ray detector and the display.

Referring now to FIGS. 1, 2 and 3, the detector assembly 16 includes a flat panel x-ray detector 14 on a first surface normally facing the x-ray source 12 and held within a supporting frame 106. The flat panel x-ray detector 14 is sized to receive a collimated beam of x-rays 104 from the x-ray source 12 and positioned immediately behind the flat panel x-ray detector 14 is a blocking lead shield 110. This may be followed by processing circuit cards 112 and 114. Following the circuit cards 12 and 114 is a flat panel display 116.

The flat panel display 116 may receive an image registered with the image received by the x-ray detector 14 for display to a human operator viewing the image from the top side of the detector assembly 16. In this configuration, the image displayed by the flat panel display 116 remains in perfect registration with the x-ray detector 14 thus eliminating confusion that can result in normal fluoroscopy systems where the image may rotate on a stationary monitor with respect to the patient as the positioner is moved. As shown in FIG. 2, in order to provide for oblique viewing angles, the flat panel display 116 may hinge upward about one of two perpendicular hinge axes 128 or 130 so as to provide better viewing for the user while still maintaining rotational registration with the patient's anatomy.

Also supported on the top side of the frame 106 is a touch screen panel 118 providing for basic level control of the x-ray system including x-ray tube voltage, exposure time, and other techniques. The front portion of the frame 106 also supports a multi-axis control handle 120 providing a number of signals depending on movement of the handle by the operator either vertically, horizontally or in rotation as shown by arrows 124 and shown also in FIG. 2. A second blocking lead shield 108 may be attached to a portion of the supporting frame 106 positioned toward the operator during normal use as shown in FIG. 1.

The circuit cards 112 provide a multiplexed signal collecting the data from the x-ray detector 12 for a central controller to be described. The circuit card 114 provides an interface for the central controller with the touch screen panel 118 and a multi-axis control handle 120.

Figure 7:
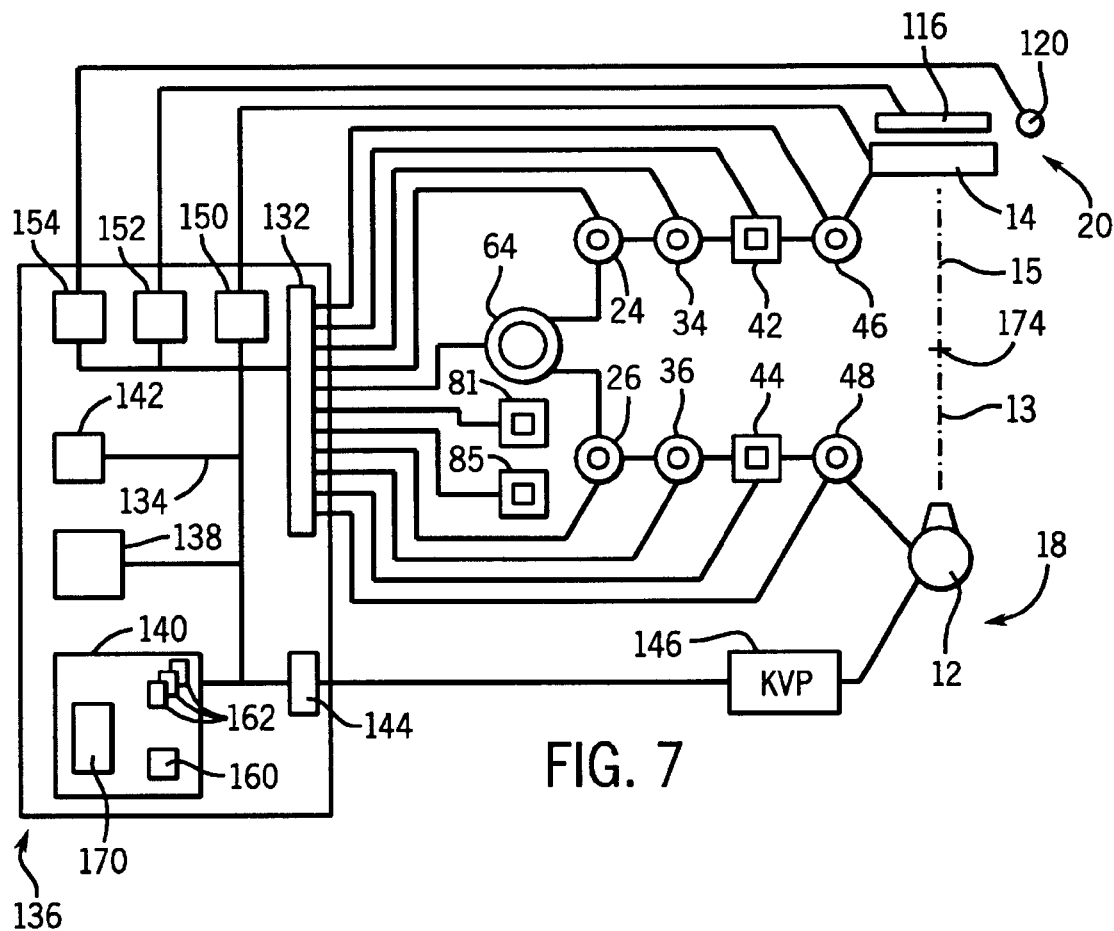
FIG. 7 is a schematic block diagram of the servo motors associated with the axis of FIGS. 1 and 6 and a controller for controlling the axes as well as the x-ray detector and x-ray source according to the present invention.

Referring now to FIG. 7, each of the different axes 24, 26, 34, 36, 42, 44, 46, 48, 64, 81, and 84 provides feedback signals and receives a command signals from an axis control interface 132 so as to provide for servo control of each axis according to techniques well known in the art. The axis control interface 132 connects to a central bus 134 of the central controller 136. The central controller 136 is constructed according to conventional computer architecture and includes a processor 138 communicating with the bus 134 and with memory 140 which may include both random access and magnetic disk memory or other mass storage devices. A network card or modem 142 also communicating with the bus provides a path for downloading of information and programs into the memory 140 from a network, such as the Internet, as will be described.

The controller 136 also provides a signal through port interface 144 (also attached to bus 134) to a high voltage power supply 146 feeding the x-ray source 12 so as to provide control over current and x-ray tube voltage and on and off duty cycle. Diagnostic signals may also be received from the power supply 146 via this port interface. Additional ports interfaces 150, 152, and 154 provide communication between the central bus 134 and the control handle 120, the x-ray detector 14, the flat panel display 116, and the touch screen panel 118 described above.

During operation, the processor 138 runs a control program 170 held in memory 140 to control the various axes 24, 26, 34, 36, 42, 44, 46, 48, 64, 81, and 84 and to control the x-ray exposure of a patient and to receive and process the image data for display on the flat panel display 116 according to commands received through the control handle 120 and touch screen panel 118.

The memory 140 may also hold a hardware configuration file 160 and one or more personality files 162. The hardware configuration file 160 stores data on the various components as shown in FIG. 6 that have been assembled together to produce the particular positioner 10. The personality files 162 contain models for how the x-ray system will operate, for example, emulating a fluoroscopy, spot film device or C-arm type configuration. Each of the personality files 162 includes a zero configuration variable describing how the positioner 10 should be initialized by movement of the axes prior to patient scan. More generally, the personality files 162 may include one or more procedures involving dynamic movement of the arms 18 and 20 for a particular procedure such as tomography. The personality files 162 also define how the control handle 120 will be interpreted to axes movement.

For example, it may be desired to operate the positioner to emulate a fluoroscopy machine with a C-arm type structure. In this case, fluoroscopy C-arm type personality files 162 would be loaded and invoked through touch screen panel 118. Generally, the C-arm emulation holds the source centerline and detector centerline in alignment as the x-ray source and x-ray detector rotate about an isocenter. Other emulations may hold the source centerline and detector centerline in alignment as the x-ray source and x-ray detector are translated.

Figure 8:
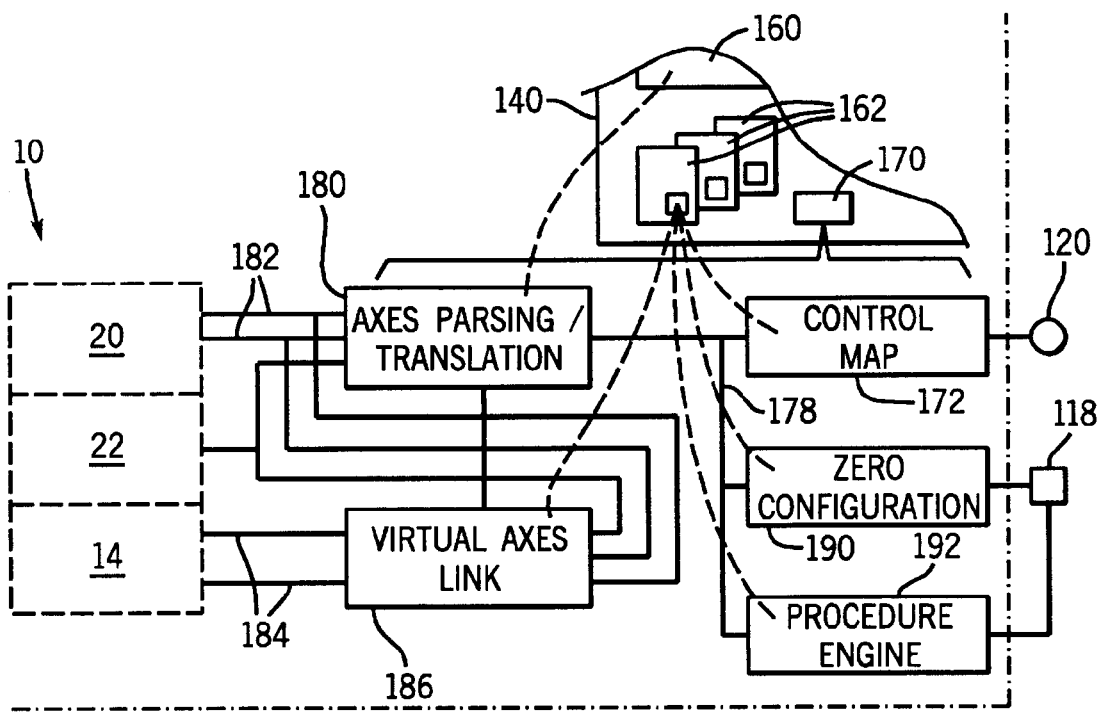
FIG. 8 is a functional diagram of tasks implemented by the controller of FIG. 7 to control the axes according to one embodiment of the invention.

Referring now to FIG. 8, the control program 170 makes use of the configuration file 160 and the personality files 162 to implement control function blocks for the operation of the positioner 10. A first function block provides a control map 172 mapping movements of the control handle 120 to movements in a room coordinate system. For example, if the positioner 10 is programmed to emulate a C-arm type device, rotation of the control handle 120 may cause angulation of the C-arm, effectively rotating the central rays 13 and 15 about a center point 174 shown in FIG. 7. The center point may be defined by the center of the base 22 or be arbitrarily located through multiple axis motion as determined by the personality file 162, as will be described. Vertical and horizontal movement of the control handle 120 may raise or move laterally the virtual C-arm simultaneously moving the x-ray source 12 and x-ray detector 14 as if they were connected by a rigid bar. Thus the complexity of possible motion of the arms 18 and 20 is simplified by the configuration file 160 to reflect the reduced freedom of motion of the machine (such as a C-arm) emulated by the positioner 10. The use of different configuration files 160, which may be freely changed, allows flexibility in changing the control mapping for different emulations or according to user preference.

The assignment of the inputs of the control handle 120 to particular motion axes is arbitrary and they may be assigned differently than described above with vertical movement of the control handle 120 changing source-to-detector distance rather than raising or lowering the x-ray detector 14 and x-ray source 12 in unison.

The control handle 120 which is fixed to the arm 20 may alternatively be used to move the arm 20 directly, by having the central controller 136 respond to control signals from the control handle 120 by energizing the appropriate axes causing the arm 20 to move in the direction of movement of the control handle 120, as if the arm 20 were being physically moved by the operator's pressure on the control handle 120. The arm 18 may operate in coordinated fashion, responding to motion of the arm 20 by a virtual axis link 186, also described below. Mass and resistance of the arms 20 and 18 to movement may be simulated by the servos on the axes.

In summary, the control map 172 produces commands 178 in room coordinates or virtual machine coordinates (the latter which describe motion of machine components, such as a C-arm, which do not in fact exist). The control map 172 may be a look-up table and interpolation rules or a set of transformation equations or the like well understood in the art. The commands 178 are received by axis parsing and translation module 180 which interrogates the hardware configuration file 160 to see what axes are available in order to realize the coordinate commands 178. Generally there will be more than one combination of different axes movements and the axis parsing and translation module 180 will select among these looking at other considerations, for example, accessibility and the avoidance of collision within the patient space.

The axis parsing and translation module 180 translates the commands 178 into positioner axes commands 182 which are provided to one of the arms, preferably 20. The second arm 18 will receive positioner axis coordinates 184 from a virtual axis link 186. The virtual axis link 186 receiving as inputs the positioner axes commands 182 from the axis parsing and translation module 180 and providing corresponding positioner axis commands 184 to achieve the desired virtual linkage between the x-ray source 12 and x-ray detector 14 as defined by the configuration file 160 and the personality files 162. Generally this linkage will amount to simulation of a virtual structure directly connecting the x-ray source 12 and x-ray detector 14 together such as a bar or C-arm or the like.

Alternatively, the commands 178 may be processed directly by the virtual axis link 186 which may provide corresponding positioner axis commands 184 to both the arms 18 and 20 whose axes are defined by the configuration file 160 and whose interaction is defined by the personality files 162.

Because the arms 18 and 20 are not directly connected by the virtual structure, a variety of other personalities may be adopted including those which provide for complex independent movement of the x-ray source 12 and x-ray detector 14 for tomography and the like requiring more complex mechanical linkage than a rigid bar. For example, in tomography, the x-ray source and x-ray detector may move in opposite directions at constant distance from a tomographic plane.

As mentioned, a zero configuration variable may be read by the control program 170 to determine the starting position of the positioner 10, e.g., whether the x-ray source 12 and x-ray detector 14 are positioned horizontally or vertically with respect to each other or laterally or for a standing patient or the like. Zero configuration task 190 handles this initialization of the axes making use of the hardware configuration file 160 and the particular machine model in personality files 162 and moving the arms 18 and 20 appropriately.

The program 170 may also implement a procedure engine 192 which records particular procedures including techniques, exposure times, motion, and positioning of the arms that may be collected and exchanged by physicians or skilled practitioners. These procedures may be invoked through the touch screen panel 118.

Referring momentarily to FIG. 7, the hardware configuration file 160, the control map 172, the zero configuration file 190, the axis parsing and translation module 180 and the various personality files 162 may be loaded via the modem 142 and thus the positioner 10 may be configured remotely and users of the positioner 10 may trade different configurations, personality modules and procedures with each other as they are developed. The ability to exchange these files, particularly on the Internet, makes it possible to develop a market in which market incentive encourage the development of procedures.

Figure 9:
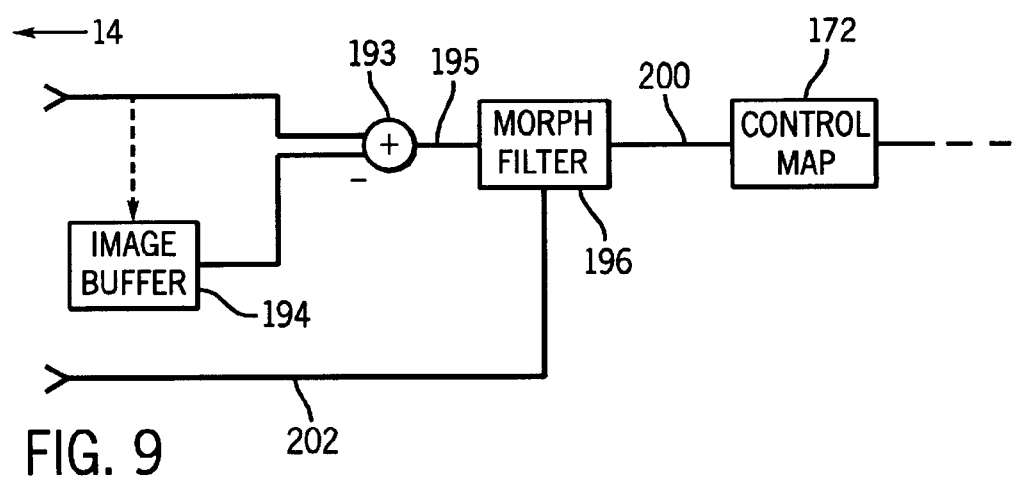
FIG. 9 is a functional diagram task implemented by the controller of FIG. 7 to automatically or semi-automatically track a bolus according to one embodiment of the invention.

Referring now to FIG. 9, one such procedure may receive image data from the x-ray detector 14 into a summing unit 193 implemented by the program 170 and also into an image buffer 194. A subtraction of a previously buffered image and the current image yields motion data 195 which may be operated on by a morphometric filter 196 to identify, for example, a moving bolus of contrast medium in certain types of studies. The morphometric filter may be initialized by user parameters 202 that may be part of a procedure engine module being one of personality files 162.

The location of the bolus relative to the position of the x-ray detector 14 may be extracted as position coordinates 200 in the room or machine frame of reference. The position coordinates 200 may be fed directly to the control map 172 so as to provide for automatic bolus tracking in which the arms 18 and 20 are automatically moved so as to maintain a bolus of contrast medium within the x-ray beam. Memory 140 may also store images including video sequences and the like, user parameter data and other data well known in the art.

Figure 10:
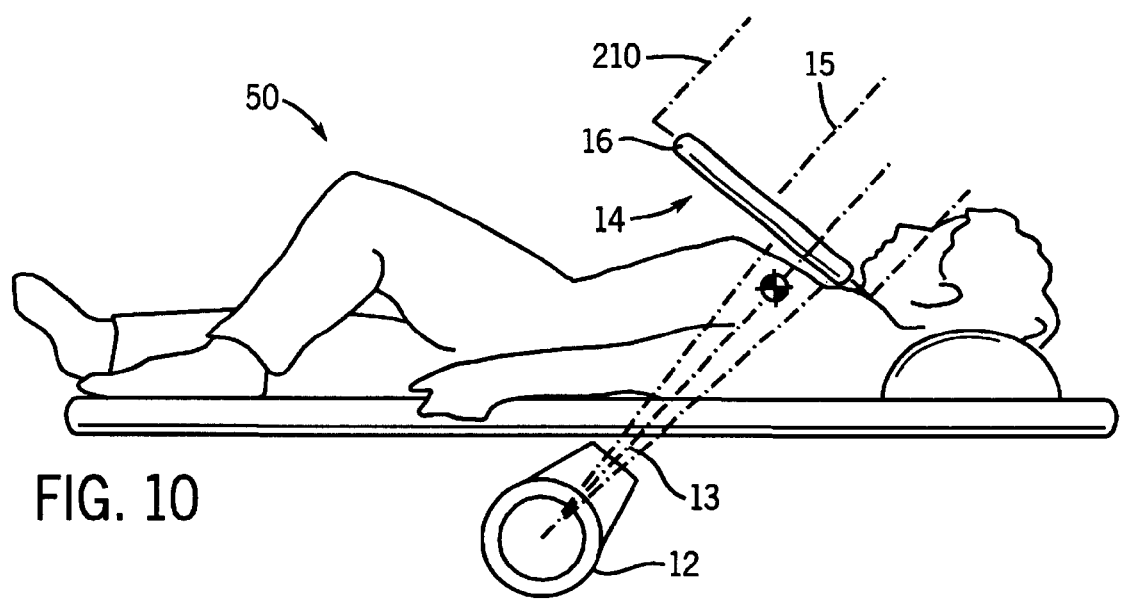
FIG. 10 is a front elevational view of a supine patient showing the x-ray detector and x-ray source positioned by the present invention in the offset opposition.

Referring now to FIG. 10, the small profile of the detector assembly 16 allows for more flexible positioning with respect to patient 50 than would be obtained with a comparable apertured image intensifier 210 shown in dotted outline. This flexibility is enhanced by the ability to offset the central ray 13 of the x-ray source 12 with respect to the axis 15 of the x-ray detector 14 by displacement of the x-ray source or by offset collimation of the x-ray beam. In either case, when a small beam of x-rays is required, that beam may be directed to a desired area of the x-ray detector 14 rather than to the center of the x-ray detector 14 and that area preferentially scanned. This capability allows improved positioning with respect to the patient 50 without obstruction by the edges of the detector assembly 16 for large apertured x-ray detectors 14 such as may be desirable in other situations.

Figure 11:
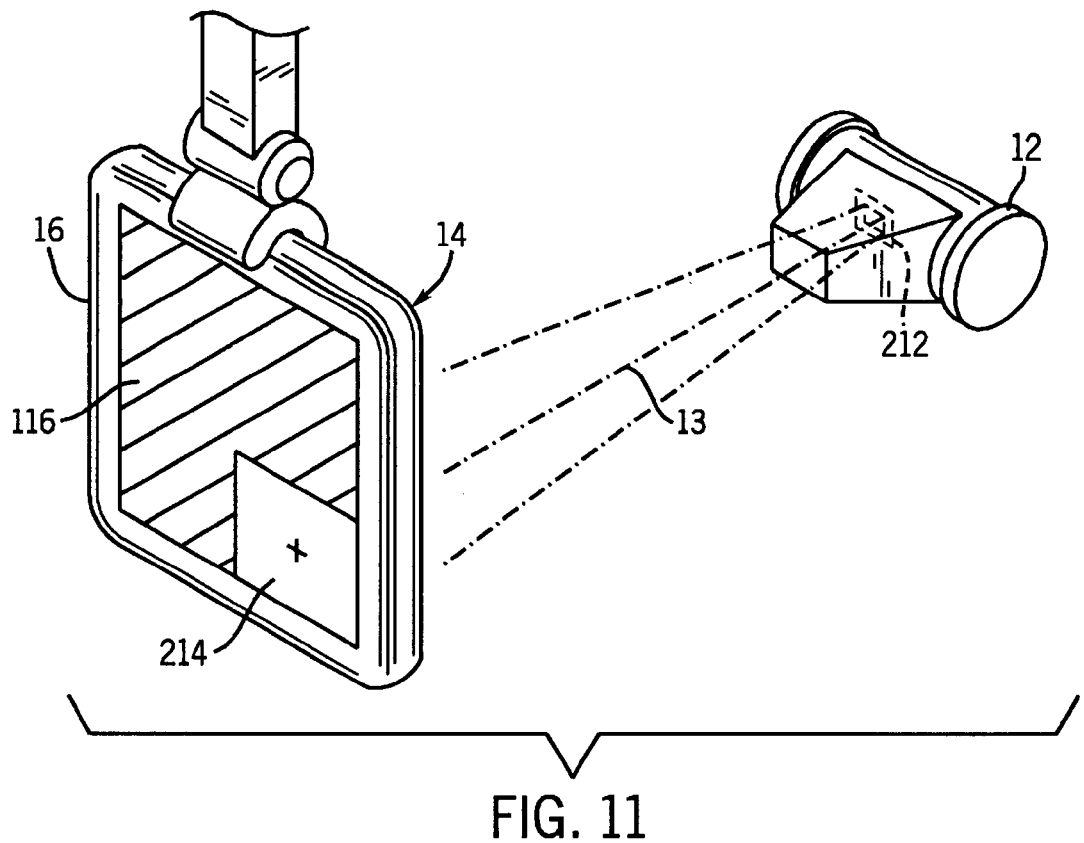
FIG. 11 is a perspective view of the x-ray detector and x-ray source of FIG. 10 showing offset collimation of the x-ray source and a region of interest display shown on the display x-ray detector assembly.

Referring to FIG. 11, as mentioned, the displacement of the central ray 13 may be performed by angulation of the x-ray source 12 through additional axes (not shown) or by adjustment of a collimator 212 to collimate the x-ray beam to less than the area of the detector but also to offset the center of the beam toward a detector edge. Control of a collimator 212 to control the exit aperture of the x-ray beam is well known in the art, and is modified only to displace the central ray 13 of the beam. Positioning of the detector assembly 16 may be enhanced by the generation of an x-ray reception pattern 214 on the face of the flat panel display 1116, showing the operator the active area of the x-ray detector 14 on the opposite side of the detector assembly 16 prior to exposure.

It is specifically intended that the present invention not be limited to the embodiments and illustrations contained herein, but that modified forms of those embodiments including portions of the embodiments and combinations of elements of different embodiments also be included as come within the scope of the following claims.

What is claimed is:

1. A multi-operating mode x-ray machine comprising:
   an x-ray source producing an x-ray beam directed along a source centerline;
   an x-ray detector detecting x-rays received along a detector centerline;
   a first and second articulated arm, the first articulated arm holding the x-ray source, the second articulated arm holding the x-ray detector, the first and second articulated arms providing for at least two axes of independent motion;
   an axis controller sending movement signals to each axis and receiving position signals from each axis to coordinate movement of the axes of the first and second arms according to a contained program, wherein the program provides a mode of operation, and
   a network interface communicating with the axis controller for receiving at least a portion of the program over a network.

2. The multi-operating mode x-ray machine of claim 1 wherein the network interface provides an interface to the Internet.

3. The multi-operating mode x-ray machine of claim 1 wherein the program portion is a machine personality defining a virtual mechanical linkage between the x-ray source and x-ray detector implemented by coordinated position signals from the axis controller to the axes of the first and second articulated arms.

4. The multi-operating mode x-ray machine of claim 3 wherein the implemented virtual mechanical linkage holds the source centerline and detector centerline in alignment as the x-ray source and x-ray detector rotate about an isocenter.

5. The multi-operating mode x-ray machine of claim 3 wherein the implemented virtual mechanical linkage holds the source centerline and detector centerline in alignment as the x-ray source and x-ray detector move perpendicular to the source and detector centerline.

6. The multi-operating mode x-ray machine of claim 3 wherein the implemented virtual mechanical linkage moves the x-ray source and x-ray detector in opposite directions at constant distance from a tomographic plane.

7. The multi-operating mode x-ray machine of claim 1 wherein the program portion is a zero configuration defining a starting position of the first and second articulated arms realized by position signals transmitted to the axes of the first and second articulated arms.

8. The multi-operating mode x-ray machine of claim 7 wherein the starting position is with the x-ray source and x-ray detector horizontally opposed at a predetermined separation distance with the source and detector centerline aligned.

9. The multi-operating mode x-ray machine of claim 7 wherein the starting position is with the x-ray source and x-ray detector vertically opposed at a predetermined separation with the source and detector centerline aligned.

10. The multi-operating mode x-ray machine of claim 1 including further a user control device communicating with the axis controller and receiving control inputs from a user to move the first and second articulated arm and wherein the portion of program is a control map translating control inputs to movement signals.

11. The multi-operating mode x-ray machine of claim 10 wherein the user control device is mounted on one of the first and second articulated arms and wherein the control inputs are received by switches activated by pressure in a desired direction of movement of the articulated arm and wherein the axis controller provides a virtual mechanical linkage between the first and second articulated arms to move both the first and second articulated arms in coordination according to the control inputs.

12. The multi-operating mode x-ray machine of claim 11 wherein the user control device is mounted on the second articulated arm.

13. The multi-operating mode x-ray machine of claim 1 wherein program portion is an axis parsing and translation file receiving control inputs and converting the control inputs to movement of the first and second articulated arms according to movement signals.

14. The multi-operating mode x-ray machine of claim 13 wherein the program portion also includes a machine personality file defining a virtual mechanical linkage between the first and second articulated arms implemented by coordinating position signals to the axes of the first and second articulated arms and wherein the axis parsing and translation table converts the control inputs to movements of the first and second articulated arms with reference to the machine personality file to preserve the virtual mechanical linkage.

15. The multi-operating mode x-ray machine of claim 13 wherein the number and type of axes of the first and second articulated arms is variable as stored in a configuration file and wherein the axis parsing and translation table converts the control inputs to movements of the first and second articulated arms to implement motion with reference to the configuration file.

16. The multi-operating mode x-ray machine of claim 13 wherein the portion of the control program received over the network includes the configuration file.

17. The multi-operating mode x-ray machine of claim 13 including further a user control device receiving control inputs from a user.

18. The multi-operating mode x-ray machine of claim 1 wherein the program portion is an x-ray procedure defining operation of the multi-operation mode x-ray machine during acquisition of x-ray data.

19. The multi-operating mode x-ray machine of claim 1 wherein the procedure defines motion over time of the x-ray source and x-ray detector during the procedure.

20. The multi-operating mode x-ray machine of claim 1 wherein the procedure defines exposure over time of the patient.

* * * * *